United States Patent [19]

Hochberg et al.

[11] Patent Number: 5,317,389
[45] Date of Patent: * May 31, 1994

[54] METHOD AND APPARATUS FOR WHITE-LIGHT DISPERSED-FRINGE INTERFEROMETRIC MEASUREMENT OF CORNEAL TOPOGRAPHY

[75] Inventors: Eric B. Hochberg, Altadena; Edmund C. Baroth, Granada Hills, both of Calif.

[73] Assignee: California Institute of Technology, Pasadena, Calif.

[*] Notice: The portion of the term of this patent subsequent to Dec. 10, 2008 has been disclaimed.

[21] Appl. No.: 530,798

[22] Filed: May 30, 1990

Related U.S. Application Data

[63] Continuation-in-part of Ser. No. 364,165, Jun. 12, 1989, Pat. No. 5,071,251.

[51] Int. Cl.$^5$ .............................................. G01B 11/06
[52] U.S. Cl. .................................. 356/382; 356/359; 356/360; 351/211; 385/43
[58] Field of Search ................... 356/382, 359, 360, 2, 356/237; 351/211, 201, 212, 221; 385/43, 116, 120

[56] References Cited

U.S. PATENT DOCUMENTS 3,781,096  12/1973  Townsley ........................... 356/382
5,071,251  12/1991  Hochberg et al. .................. 356/359

OTHER PUBLICATIONS

PCT Publication, WO90/12534, Publication Date Nov. 1, 1990, Glynn et al.; title: Device for Monitoring Body Functions.

*Primary Examiner*—Samuel A. Turner
*Assistant Examiner*—LaCharles P. Keesee, II
*Attorney, Agent, or Firm*—Leonard Tachner

[57] ABSTRACT

An novel interferometric apparatus and method for measuring the topography of aspheric surfaces, without requiring any form of scanning or phase shifting. The apparatus and method of the present invention utilize a white-light interferometer, such as a white-light Twyman-Green interferometer, combined with a means for dispersing a polychromatic interference pattern, using a fiber-optic bundle and a disperser such as a prism for determining the monochromatic spectral intensities of the polychromatic interference pattern which intensities uniquely define the optical path differences or OPD between the surface under test and a reference surface such as a reference sphere. Consequently, the present invention comprises a "snapshot" approach to measuring aspheric surface topographies such as the human cornea, thereby obviating vibration sensitive scanning which would otherwise reduce the accuracy of the measurement. The invention utilizes a polychromatic interference pattern in the pupil image plane, which is dispersed on a point-wise basis, by using a special area-to-line fiber-optic manifold, onto a CCD or other type detector comprising a plurality of columns of pixels. Each such column is dedicated to a single point of the fringe pattern for enabling determination of the spectral content of the pattern. The auto-correlation of the dispersed spectrum of the fringe pattern is uniquely characteristic of a particular optical path difference between the surface under test and a reference surface.

20 Claims, 3 Drawing Sheets

METHOD AND APPARATUS FOR WHITE-LIGHT DISPERSED-FRINGE INTERFEROMETRIC MEASUREMENT OF CORNEAL TOPOGRAPHY

ORIGIN OF INVENTION

The invention described herein was made in the performance of work under NASA Contract No. NAS-7-918 and is subject to the provisions of Public Law 96-517 (35 USC 202) in which the Contractor has elected to retain title.

CROSS REFERENCE TO RELATED APPLICATIONS

This application is a continuation-in-part of U.S. patent application Ser. No. 07/364,165 filed Jun. 12, 1989 now U.S. Pat. No. 5,071,251.

TECHNICAL FIELD

The present invention relates generally to an interferometric method and apparatus for measuring corneal topography and more specifically, to an apparatus and method in which a white-light interferometer generates a polychromatic fringe pattern. A fiber-optic manifold and an optical disperser separate this fringe pattern into its monochromatic constituent fringe patterns. These constituent fringe patterns uniquely define the optical path differences between the surface under test and a reference surface whereby the topography of the surface under test, such as a human cornea, may be defined without requiring the use of scanning, which would otherwise reduce the accuracy of the measurement.

BACKGROUND ART

Corneal surgery is currently undergoing rapid evolution with improvements designed to minimize or eliminate astigmatism following penetrating keraplasty (corneal transplants), as well as to correct refractive error. Because the cornea is the most powerful refracting surface of the eye, numerous procedures have been devised to incise, lathe, freeze, burn and reset the cornea to alter its shape. Currently practiced keratorefractive surgical techniques include: cryorefractive techniques (keratomileusis, keratophakis, ipikeratophakia), radial keratotomy, thermal keratoplasty, corneal relaxing incisions and wedge resections.

When preparing the patient for any of these surgical techniques, it is essential to accurately measure the corneal curvature. Existing methods to measure corneal curvature include central keratometry and photokeratoscopy with central keratometry. However, with these methods the diameter of the cornea that can be accurately measured is limited. Recently, photokeratoscopy has been adapted to provide a topographic map of the cornea. However, existing keratometers are limited in two important regards. Firstly, these instruments are predicated on geometrical image forming principles and assume the corneal topography can be expressed in terms of zones of various spherical radii. This in turn involves assumptions as to the nature of the surface under test. With more strongly aspheric corneas or as larger areas on even the average or typical size cornea are considered, the measurement becomes extremely ambiguous. Secondly, primarily as a consequence of the above, but also because of optical engineering considerations, most instruments are limited in terms of the aperture of the cornea that can be measured. Existing instruments typically cover corneal diameters no greater than three millimeters.

It is recognized that optical interferometric techniques for non-invasive measurement of corneal topography provides a way of producing a contour map of the corneal surface directly. A suitable achromatic or white-light interferometer is disclosed in co-pending patent application, Ser. No. 07/364,165, filed Jun. 12, 1989 and of which this application constitutes a continuation-in-part. However, a disadvantage of prior art interferometric corneal mapping devices is the requirement for a scanning operation in order to have sufficient phase information for mapping the entire surface of the cornea. This means that the cornea must be stationary during the scanning process. If the scanning can be performed faster than typical eye movements, that difficulty can be overcome. However, a technique that does not require scanning and captures the topographical information in one short duration exposure would be preferable. Thus, there is an ongoing need for a real-time "snapshot" keratometer system for medical diagnosis and for preparation of a corneal contour for eye surgery, as well as for post-operative analysis of completed eye surgery.

SUMMARY OF THE INVENTION

The present invention solves the aforementioned need by providing an apparatus and method for generating topographical information in one exposure or "snapshot", thereby obviating any requirement for scanning and thereby significantly improving the opportunity for an accurate mapping of the corneal shape. The invention forms a polychromatic interference pattern in a pupil image plane, followed by a special area-to-line fiber optic manifold, followed by dispersing means and a CCD or other type detector comprising a plurality of columns of pixels. The terms "polychromatic" and "white-light" are used herein interchangeably and are intended to refer to multiple or a continuum of wavelengths of light over a given bandwidth. Each such column is dedicated to a single sample of the fringe pattern for enabling determination of the intensity of each spectral component of the pattern at that sample point. The autocorrelation of the dispersed spectrum of the polychromatic fringe pattern is uniquely characteristic of a particular optical path difference between the surface under test and a reference surface. Consequently, by knowing the intensity value of the spectral components making up the polychromatic fringe intensity, it is possible to determine the precise surface height at each particular point being mapped onto a column of pixels. Consequently, a collection of columns permits analysis of the spectral characteristics of the fringe pattern at a collection of points, so that the surface height of the cornea or other aspheric lens being tested can be determined at each such point. A fiber optic bundle or manifold is employed to conduct light in the pupil image plane to the dispersing means. The bundle comprises a collection of fibers arranged in a two-dimensional array at the input end (the end which samples the polychromatic fringe intensities in the pupil image plane) and a one-dimensional array at the output end where the polychromatic output will be dispersed. Thus, the present invention permits the generation of phase values or surface heights at each dispersed point with a single exposure, that is, without vibration-sensitive scanning or phase shifting.

In order to exploit this white-light technique, the interferometer must be properly achromatized, that is, it must be capable of preserving the wavefront quality in all wavelengths of light used in the test over a given bandwidth. One such achromatized interferometer is disclosed in the parent U.S. application, Ser. No. 07/364,165 wherein a preferred embodiment of such an interferometer comprises three off axis parabolas. The first such parabola acts as a collimator, the second forms a spherical wavefront converging on the cornea and following the second reflection, preserves the optical path differences of the aberrated wavefront. The third parabola forms an image of the cornea. These three parabolic reflecting surfaces are arranged in conjunction with a beam splitter and a reference mirror to form a Twyman-Green type interferometer. However, in the present invention, this white-light interferometer is combined with an area-to-line fiber-optic manifold, a disperser and a detector array such as a CCD detector array. This unique combination produces the requisite fringe data instantaneously, that is, in one "snapshot" image for measuring the topography of the aspheric surface such as the human eye cornea, without requiring any form of scanning. The detailed aspects of the method and apparatus of the present invention will be disclosed hereinafter in more detail. However, it should be understood that while the particular embodiment of the invention disclosed herein is shown for use in measuring the contour of the cornea of the human eye, it will be understood that the unique fidelity preservation characteristics of the interferometer and the unique "snapshot" characteristics of the combination of the interferometer and the dispersion techniques herein described, permit measurement of any aspheric surface at virtually any wavelength or bandwidth. Thus for example, the present invention is useful in the measurement of aspheric surface characteristics of mirrors, such as mirrors that may be used in telescopes. It will be understood that because of the highly desirable "snapshot" characteristic of the present invention which obviates the requirement for scanning using more conventional interferometric techniques, the present invention is particularly advantageous when used for mapping the corneal surface.

OBJECTS OF THE INVENTION

It is therefore a principal object of the present invention to provide an apparatus and method for topographically mapping an aspheric surface, wherein a single interference pattern image provides all the requisite information.

It is an additional object of the present invention to provide a dispersed-fringe white-light interferometric apparatus and method which combine a unique achromatic optical interferometer with spectral component dispersion for uniquely identifying the optical path difference between an aspheric surface and a reference surface in a single "snapshot" image.

It is still an additional object of the present invention to provide an apparatus and method for mapping the human cornea in a substantially instantaneous imaging process, thereby enhancing the accuracy of the measurement as compared with those processes which require scanning the cornea over a period of time.

It is still an additional object of the present invention to provide an apparatus and method for measuring the topography of an aspheric surface, utilizing an achromatized Twyman-Green interferometer, a fiber-optic bundle for conveying the reflected light from a plurality of points on the surface under test to a disperser for spectrally separating a white-light fringe pattern into its spectral components, a detector array and autocorrelation of the white-light fringe pattern for uniquely identifying the optical path differences between the surface under test and a reference surface for each such point.

BRIEF DESCRIPTION OF THE DRAWINGS

The aforementioned advantages and objects of the present invention, as well as additional objects and advantages thereof, will be more fully understood hereinafter as a result of a detailed description of a preferred embodiment when taken in conjunction with the following drawings in which.

DETAILED DESCRIPTION OF A PREFERRED EMBODIMENT

Description of the Invention

Figure 1:
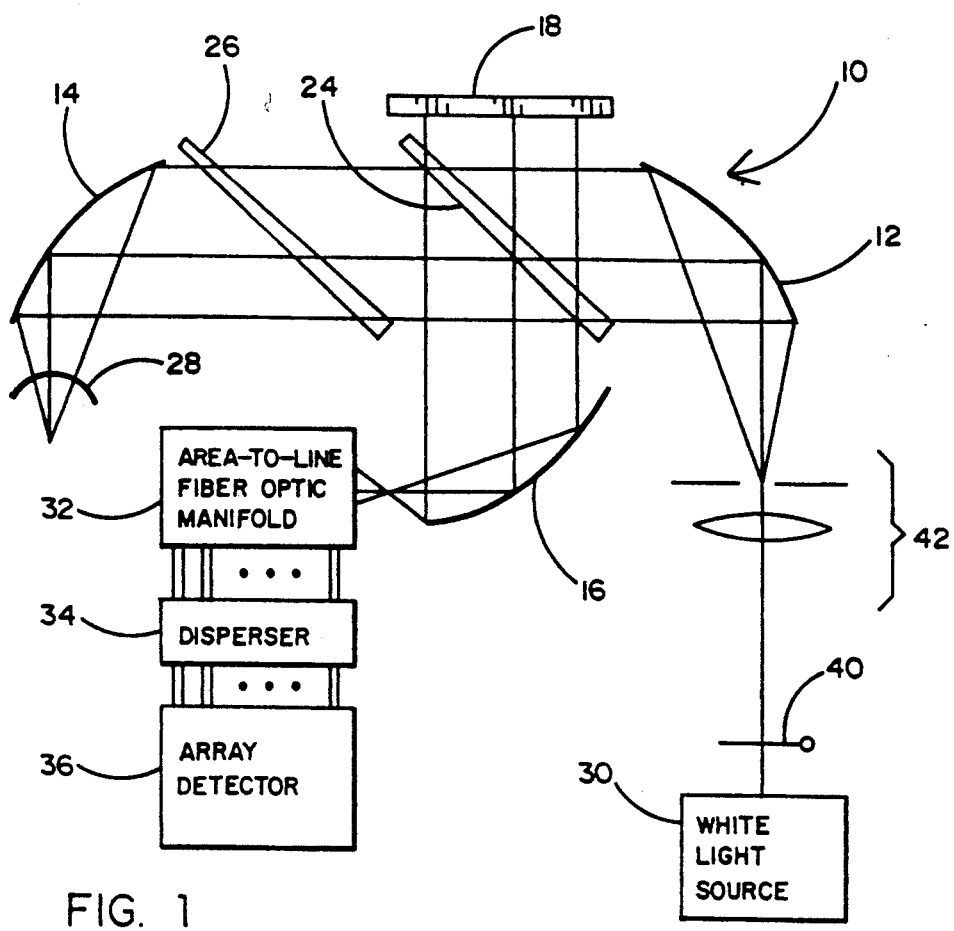
FIG. 1 is a combined optical ray and block diagram of an apparatus of the present invention.
Figure 2:
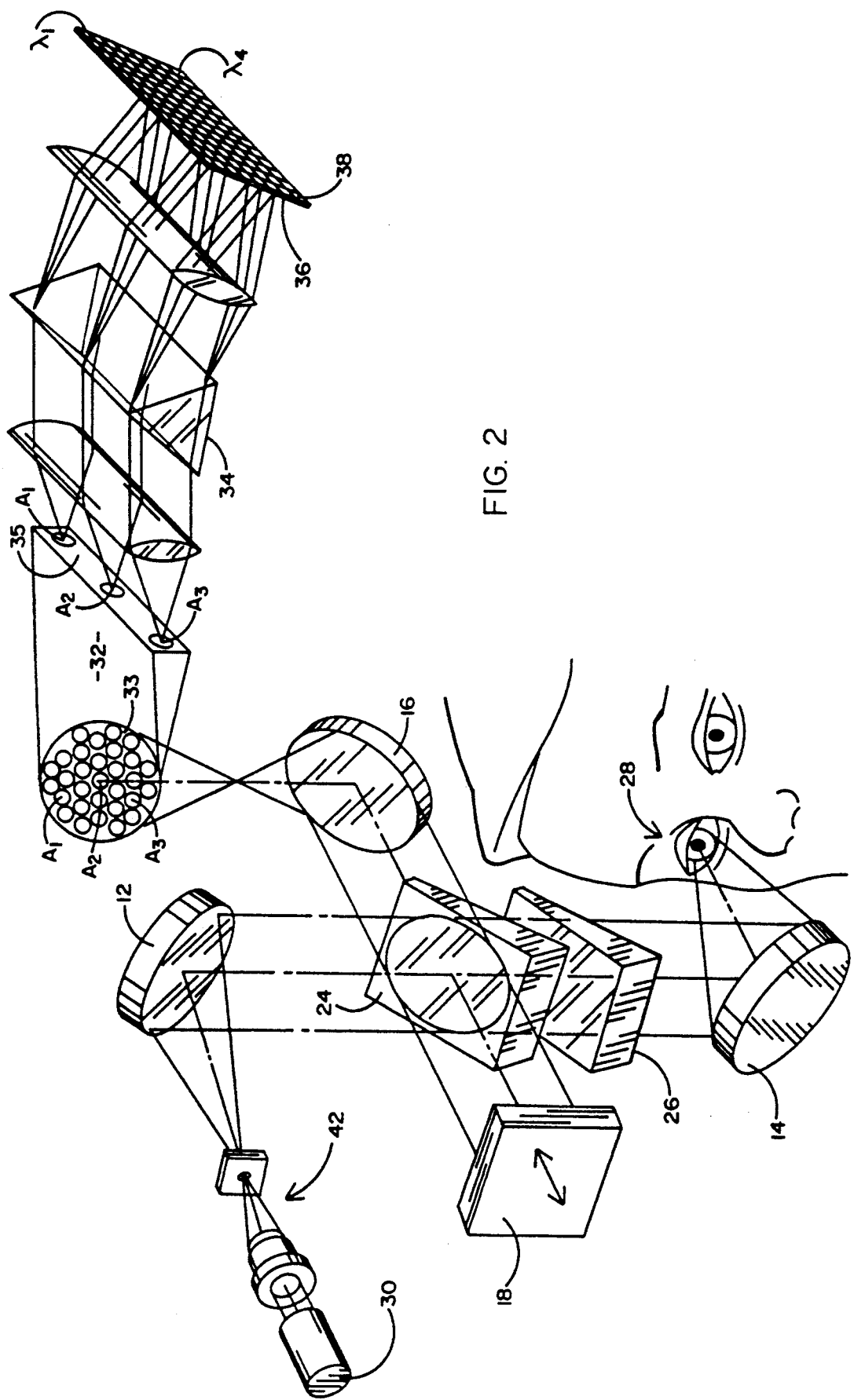
FIG. 2 is a representation of the physical components of the present invention shown in use for measuring the topography of the human cornea.

Referring now to FIGS. 1 and 2, it will be seen that the white-light dispersed-fringe interferometer 10 of the present invention comprises a parabolic beam collimator surface 12, a parabolic focusing surface 14, a parabolic imaging surface 16, a reference reflecting mirror 18, a beam splitter 24 and a compensator 26. Also provided for use with interferometer 10 are a white-light source 30, an area-to-line fiber-optic manifold 32, a disperser 34 and a detector array 36.

White-light source 30 presents a point source of white-light at the focal point of parabolic beam collimator surface 12. This is accomplished by utilizing a shutter 40 and a microscope objective beam expander and spatial filter 42, both of which act upon the light beam emanating from white-light source 30.

The function of collimator 12 is to provide a collimated wave-front which travels from right to left, as seen in FIG. 1. A selected fraction of this collimated wavefront of light is passed through a beam splitter 24, which is preferably of a wedged, coated glass configuration and which provides an optimum equivalent single surface beam splitter characteristic. The light passing through the beam splitter to the left of FIG. 1, impinges upon parabolic focusing surface 14 which focuses the reflected light nominally on the center of curvature of the surface to be measured. The light reflected from the cornea or other aspheric surface, nominally retraces the path of the incident light in the reverse direction up to the beam splitter 24 where it is reflected downwardly (as seen in FIG. 1) onto the parabolic imaging surface 16.

That portion of the collimated light traveling from right to left as shown in FIG. 1, which is not transmitted by the beam splitter, but is instead reflected thereby, impinges upon a plano reference mirror 18 which is positioned and oriented properly to provide a plano reference wavefront which is made to interfere with the light reflected from the cornea 28. Compensator 26 comprises a beam splitter compensator plate which is identical in shape to beam splitter 24, but which is transparent and thus provides path length compensation so that the light traveling to and from the cornea will pass through the same thickness of the same material as the light reflected to the mirror 18, which is, in turn, reflected back through the beam splitter 24.

The focal length and F-number of the parabolic reflecting surfaces 14 and 16, should be the same and should be selected to provide focal lengths commensurate with the size and general shape of the aspheric surface to be mapped. In the case of a human cornea, it has been found desirable to use an F-number equal to about 1.0 for each of the parabolic reflecting surfaces. In most applications for aspherical surface measurement for which the present invention may be used, the F-number of the parabolic reflecting surfaces 14 and 16 is contemplated to be within the range of 0.6 and 20.0. The F-number of surface 12 does not necessarily have to be equal to the F-number of the other two parabolic surfaces, but is, for practical size and scaling purposes, likely to be in the same range.

The resulting white-light interferometric fringe pattern is reflected by parabolic reflecting surface 16 onto an area-to-line fiber-optic bundle or manifold 32. The function of manifold 32 is to rearrange points or pixels of the white-light fringe pattern from a two-dimensional array to a linear array. Accordingly, manifold 32 has a first surface 33 in which the bundle of optical fibers are arranged, for example, as shown in FIG. 2, in a hexagonally packed array of approximately the size of the image reflected by parabolic surface 16. Furthermore, manifold 32 has a second surface 35, in which the opposite ends of the same optical fibers are arranged in a line or linear array, so that there is a beam of light emanating from surface 35 for each optical fiber positioned at surface 33. Each such beam of light (the intensity of which depends on the local fringe pattern features) corresponds to a single point or pixel and registers the total white-light fringe intensity at that point or pixel, depending upon the optical path difference between the cornea 28 and a reference surface that effectively created by the reference mirror 18.

Figure 3:
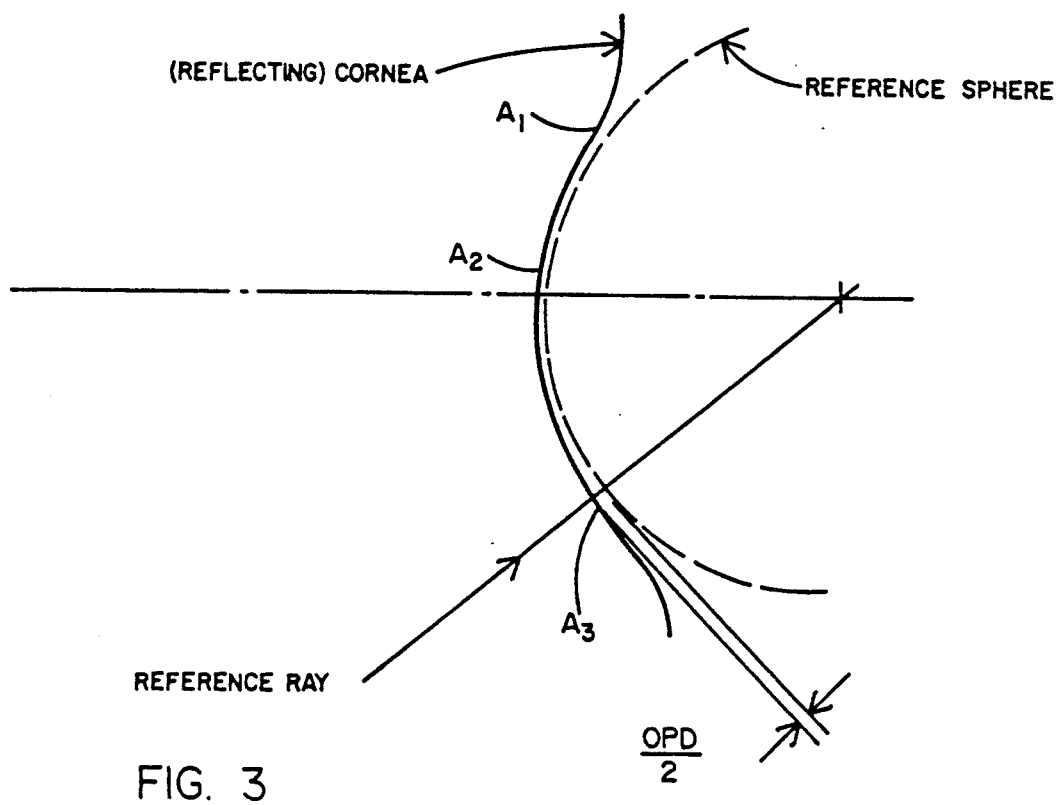
FIG. 3 is a schematic illustration of optical path differences between the cornea and a reference sphere.

The linear array of optical fibers at surface 35 of manifold 32 is positioned adjacent a disperser 34, which may for example be in the form of an elongated prism. The purpose of disperser 34 is to disperse the white-light emerging from the two-dimensional array-end 33 of the fiber bundle, so that on the other side of the same prism, the light is angularly deviated according to wavelength. Each such wavelength-dispersed light beam is incident on a column of detectors 38 on a detector array 36, which may for example be a charge coupled device detector array. It will be seen hereinafter that the purpose of disperser 34 and detector array 36 is to facilitate essentially instantaneous measurement of the spectral components of the white-light interferometric fringe pattern at each point corresponding to a single optical fiber at surface 33 of manifold 32. By dispersing the total white-light fringe intensity into its individual spectral components, it is possible to calculate a unique OPD or Optical Path Difference, using a single "snapshot" interferometric image, where OPD is defined in FIG. 3.

To further illustrate the function of the fiber-optic bundle 32, the disperser 34 and the detector array 36, reference, is again made to FIG. 2. As shown therein, three exemplary points or pixels, A1, A2 and A3 at the surface 33, correspond to three distinct points of OPD measurement, namely those same three points identified in FIG. 3. Each pixel, A1, A2 and A3 has associated with it a single fiber in the fiber-optic bundle 32 which terminates at the opposite end of the fiber-optic bundle 32 at surface 35, adjacent one side of disperser 34. Due to the well-known behavior of prisms in regard to the dispersion of different wavelengths of light passing therethrough, the opposite side of prism 34 produces three respective dispersed images falling on three columns of detectors 38. Detectors 38 are arranged relative to the dispersed image for each of points A1, A2 and A3 so that at one end of the linear array of detectors, the intensity of the highest frequency or shortest wavelength signal is detected, namely corresponding to wavelength $\lambda_1$ and at the other end, the intensity of the lowest frequency or longest wavelength frequency is detected, namely corresponding to wavelength $\lambda_4$.

Figure 4:
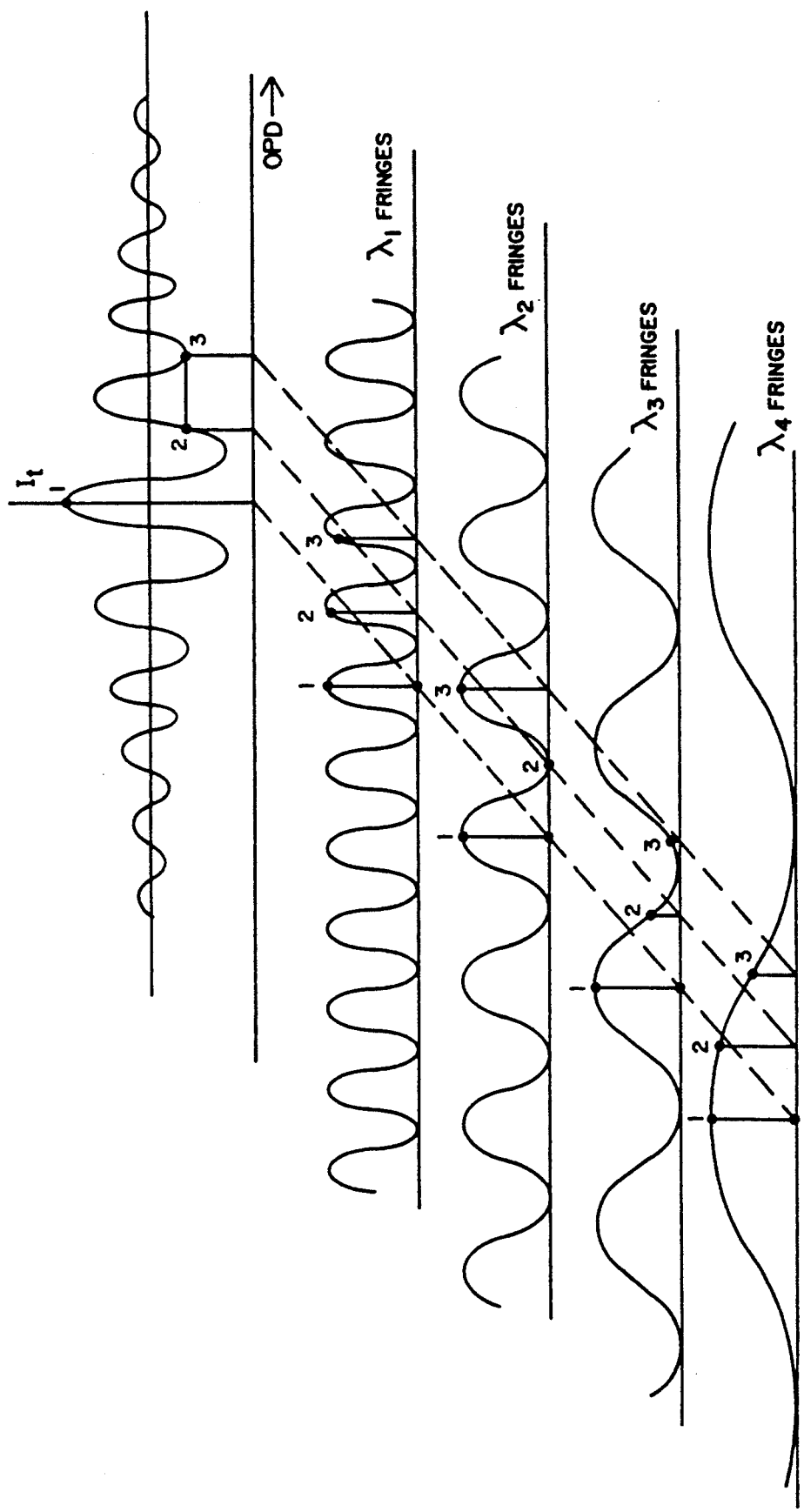
FIG. 4 is a graphical representation of the white-light intensity characteristic of the present invention, as well as its individual spectral components in a typical application.

The reason for dispersing the intensity pattern image at each point A1, A2 and A3 is to provide a unique indication of OPD for each such point. The need for separate frequency spectral components of the fringe pattern is illustrated in FIG. 4. As seen in the top-most graph of FIG. 4, if one were to plot image intensity as a function of OPD, without more information, the result is ambiguous. The maximum intensity at zero OPD occurs at point 1 but, points 2 and 3, while corresponding to different OPD's, have precisely the same total white-light intensity. Thus, if for example, point A1 were to register a white-light intensity, corresponding to either point 2 or point 3, its OPD or path length difference between the cornea or other aspheric surface under test on the reference surface, could be either one of at least two distinct values.

On the other hand, it will be observed that if the white-light intensity graph of FIG. 4 is broken down for example into four distinct spectral components corresponding to the lower four graphs of FIG. 4, the individual spectral components corresponding to each point 2 and 3 are different. Thus for example, point 1 on the white-light intensity graph of FIG. 4 corresponds to the sum of the individual spectral components at point 2. Similarly, the white-light intensity at point 3 in the upper graph of FIG. 4 corresponds to the sum of the individual spectral component points 3 in the graphs of $\lambda_1$, $\lambda_2$, $\lambda_3$ and $\lambda_4$ fringes. It can be seen therefore that if the fringe spectral components are known, the individual values of OPD can be uniquely identified for each set of such spectral components at the particular point, 1, 2, or 3 or other such points in the graphs of FIG. 4.

Thus, it will be seen that by combining an achromatic interferometer with a special area-to-line fiber-optic bundle and a plurality of rows and columns of detector pixels, one can generate phase values or surface heights at each dispersed point with a single exposure, that is, without vibration-sensitive scanning or phase shifting. One requirement is that the surface slope conjugate to the fiber aperture at each such point be less than a quarter-wave height change over the aperture. Relatively sparse sampling of the surface under test is the price one pays for this "snapshot" approach. Instead of points in the two-dimensional test pupil mapping onto a two-dimensional detector array, one of the dimensions (e.g. the columns of the array) must be preserved for dispersion. Not surprisingly, this technique presents trade-offs between the number of samples, resolution or sensitivity (OPD uncertainty), and dynamic range (maximum OPD). A first-order analysis of these tradeoffs follows:

FIRST-ORDER PARAMETRIC ANALYSIS

Compared to a monochromatic interferometer of wavelength $\lambda$, a polychromatic interferometer with spectral bandpass $BP = \lambda_{max} - \lambda_{min}$ has fundamental resolution given by:

$$\text{fundamental } OPD\text{resolution} = \lambda_{min}\lambda_{max}/BP \quad (1)$$

From the above we see how with large bandpass the fundamental resolution is comparable to the shortest wavelength present in the source spectrum.

With sufficiently high S/N, i.e., sufficient source brightness, low photometric and electronic noise, low digitization errors and high radiometric efficiency, fractional-wavelength sensitivity is possible, just as in monochromatic interferometric techniques. Allowing sub-fringe resolution then, we may enhance the above by a factor $a$ where $a<1$:

$$OPD\text{resolution} = a[\lambda_{min} + \lambda^2_{min}/BP] \quad (2)$$

To estimate fundamental and practical resolution capabilities, we consider the resolution associated with a polychromatic system spanning the sensitivity band of a silicon detector, namely 0.4 microns to 1.0 microns (BP=0.6 microns.) Thus, $$OPD\text{resolution} = a[0.4 + (0.4 \times 0.4/0.6)] = 0.67 \, a \text{ microns.} \quad (3)$$

The above result gives the basic sensitivity scale of a polychromatic interferometer operating over the maximum useful bandpass of a silicon detector. Clearly, reducing the bandpass will "desensitize" the instrument and thereby allow some combination of improved sampling or increased maximum OPD performance.

Equation 2 may be re-arranged for BP (OPD resolution):

$$BP(OPD\text{resolution},a) = \lambda_{min}/\{(OPD\text{resolution}/a\lambda_{min}) - 1\} \quad (4)$$

Dispersing the spectral bandpass BP linearly over N pixels in an array detector means the width of a spectral bin is:

$$\Delta\lambda = BP/N \quad (5)$$

The above dispersion will determine the maximum OPD=OPDmax that can be handled by this approach according to:

$$OPD\text{max} = \lambda^2/\Delta\lambda = N\lambda^2/BP \quad (6)$$

For the most conservative estimate of OPDmax, use $\lambda_{min}$ for $\lambda$ above; to wit:

$$OPD\text{max} = \lambda_{min}^2/\Delta\lambda = N\lambda_{min}^2/BP \quad (7)$$

Rearranging to solve for N(OPDmax) . . .

$$N(OPD\text{max}) = BP \times OPD\text{max}/\lambda_{min}^2 \quad (8)$$

Again considering the full 0.6 micron BP associated with a silicon detector, how many pixels or spectral bins are required to handle an OPDmax requirement of 40 microns?

$$N(OPD\text{max}) = BP \times OPD\text{max}/\text{lmin2} = 0.6 \times 0.4/0.4 \times$$

$$0.4 = 150 \text{ bins each } 0.6/150 = 4\text{nm} = 40\text{Å wide.}$$

Given an $A \times B$ detector array, and having to devote N spectral pixels to each measurement point in the test pupil, the number of samples S supported by an $A \times B$ array is:

$$S = AB/N \quad (9)$$

Thus, using a 0.6 micron BP and accommodating 40 micron maximum OPD (with 0.67 micron fundamental sensitivity) the number of samples supported by various detectors is:

$S = 512 \times 512/150 = 1,747$ samples or, a $41 \times 41$ array of samples given a $512 \times 512$ element detector.

$S = 1000 \times 1000/150 = 6,667$ samples or, a $82 \times 82$ array of samples given a $1000 \times 1000$ element detector.

Note that for the $512 \times 512$ element detector $512/150 \approx 4$ parallel dispersion channels will be required and $\sim 7$ parallel dispersion channels are required for the $1000 \times 1000$ element detector.

CONCLUSIONS

The following are the most attractive features of the invention:

1) reduced sensitivity to vibrating or uncooperative elements;
2) absolute topography of discontinuous surfaces;
3) variable topographic sensitivity, spatial sampling, dynamic range.

The method and apparatus of the present invention may be applied to the problem of corneal topography where 20 micron-class measurements can be supported on a $74 \times 74$ array of samples using a $256 \times 256$ element (commonly available CCD) detector. Sub-micron sensitivity-class measurements can be provided over a $41 \times 41$ sample array using $512 \times 512$ element array.

It will now be understood that what has been disclosed herein comprises a novel interferometric apparatus and method for measuring the topography of aspheric surfaces, without requiring any form of scanning or phase shifting. The apparatus and method of the present invention utilize a white-light interferometer, such as a white-light Twyman-Green interferometer, combined with a means for dispersing a polychromatic interference pattern, using a fiber-optic bundle and a disperser such as a prism for determining the spectral components of the polychromatic interference pattern. These components uniquely define the optical path differences or OPD between the surface under test and a reference surface such as a reference sphere. Consequently, the present invention comprises a "snapshot" approach to measuring aspheric surface topographies such as the human cornea, thereby obviating the prior art requirement for vibration sensitive scanning which would otherwise reduce the accuracy of the measurement.

Those having skill in the art to which the present invention pertains, will now as a result of the applicants' teaching herein, perceive various modifications and additions which may be made to the invention. By way of example, the precise range of wavelengths to be used herein, as well as the precise sensitivity, resolution and dynamic range of the measurement herein described, may be varied depending upon the application. Furthermore, it should be understood that although the present invention has been described primarily for use in mapping the topography of the human cornea, the invention may be readily applied for measuring the topography or wavefront quality of virtually any wavefront with appropriate variation in parameters for obtaining the required sensitivity, resolution and dynamic range for such wavefront. Accordingly, all such modifications and additions are deemed to be within the scope of the invention, which is to be limited only by the claims appended hereto.

We claim:

1. An apparatus for mapping the topography of an aspheric surface; the apparatus comprising:
    a white-light interferometer for generating a polychromatic interferometric fringe pattern, said fringe pattern corresponding to the optical path differences between said aspheric surface and a reference surface of known topography; and
    means for determining monochromatic fringe pattern components of said polychromatic fringe pattern for unambiguously measuring said optical path differences from a single interferometric image.

2. The apparatus recited in claim 1 wherein said determining means comprises an optical fiber manifold having a two-dimensional array of optical fibers at a first end and a linear array of said optical fibers at a second end; said first end of said fiber manifold being disposed for receiving said polychromatic fringe pattern;
    a disperser positioned adjacent said second end of said optical fiber manifold, said disperser providing dispersion of said polychromatic fringe pattern in proportion to wavelength; and
    a detector array positioned relative to said disperser for detecting said monochromatic fringe pattern components.

3. The apparatus recited in claim 2 wherein said detector array comprises a plurality of detectors arranged in rows and columns, the detectors associated with each respective column being devoted to determining the monochromatic fringe pattern components at a respective one of said optical fibers.

4. The apparatus recited in claim 2 wherein each of said optical fibers is associated with a distinct location on said aspheric surface.

5. The apparatus recited in claim 2 wherein said disperser comprises a prism.

6. The apparatus recited in claim 1 wherein said interferometer is a Twyman-Green interferometer.

7. The apparatus recited in claim 1 wherein said aspheric surface is a human cornea.

8. A keratometer for measuring the shape of the surface of a cornea; the keratometer comprising:
    an interferometer for generating a polychromatic interferometric fringe pattern corresponding to optical path differences between said cornea surface and a reference surface of known shape; and
    means for generating monochromatic fringe pattern intensities of said polychromatic fringe pattern for unambiguously measuring said optical path differences from a single interferometric image.

9. The keratometer recited in claim 8 wherein said generating means comprises an optical fiber manifold having a two-dimensional array of optical fibers at a first end and a linear array of said optical fibers at a second end; said first end of said fiber manifold being disposed for receiving said polychromatic fringe intensity;
    a disperser positioned adjacent said second end of said optical fiber manifold, said disperser providing dispersion of said polychromatic fringe intensity in proportion to wavelength; and
    a detector array positioned relative to said disperser for detecting said monochromatic fringe pattern intensities.

10. The keratometer recited in claim 9 wherein said detector array comprises a plurality of detectors arranged in rows and columns, the detectors associated with each respective column being devoted to determining the monochromatic fringe pattern intensities at a respective one of said optical fibers.

11. The keratometer recited in claim 9 wherein each of said optical fibers is associated with a distinct location on said cornea surface.

12. The keratometer recited in claim 9 wherein said disperser comprises a prism.

13. The keratometer recited in claim 8 wherein said interferometer is a Twyman-Green interferometer.

14. A method for mapping the topography of an aspheric surface; the method comprising the steps of:
    a) generating a polychromatic interferometric fringe pattern corresponding to the optical path differences between said aspheric surface and a reference surface of known topography;
    b) determining monochromatic fringe pattern intensities of said polychromatic fringe pattern; and
    c) calculating said optical path differences from said monochromatic fringe pattern intensities.

15. The method recited in claim 14 wherein step b) comprises the steps of:
    b1) converting said polychromatic fringe pattern into a linear array of pattern image points;
    b2) dispersing each said image point to form a plurality of substantially monochromatic images; and
    b3) detecting said dispersed monochromatic images of each said image point to construct the monochromatic fringe pattern intensities of said polychromatic fringe pattern.

16. The method recited in claim 15 wherein step b1) comprises the steps of:
    b1-1) directing discrete portions of said polychromatic fringe pattern into respective first ends of a plurality of optical fibers, the respective first ends of said fibers being arrayed to sample substantially the entire aspheric surface; and
    b1-2) arranging the respective second ends of said fibers to form a linear array.

17. The method recited in claim 16 wherein step b2) comprises the step of passing light, emanating from said respective second ends of said fibers, through a prism.

18. The method recited in claim 15 wherein step b3) comprises the step of providing an array of detectors arranged in rows and columns, the detectors associated with each respective column being devoted to determining the monochromatic intensities corresponding to a respective one of said pattern image points.

19. A method for measuring the shape of a corneal surface; the method comprising the steps of:
    a) generating a polychromatic interferometric fringe pattern corresponding to the optical path differences between said corneal surface and a reference surface of known topography;
    b) determining monochromatic fringe pattern intensities of said polychromatic fringe pattern; and c) calculating said optical path differences from said monochromatic fringe pattern intensities.

20. The method recited in claim 19 wherein step b) comprises the steps of:

b1) converting a two-dimensional array of sample points of said polychromatic fringe pattern into a one-dimensional array of pattern image sample points;

b2) dispersing each said image sample point to form a plurality of substantially monochromatic intensities; and b3) detecting said dispersed monochromatic intensities of each said image sample point to construct the constituent monochromatic fringe pattern components of said polychromatic fringe pattern.

* * * * *